United States Patent

Scafetta et al.

[11] Patent Number: 5,925,369
[45] Date of Patent: Jul. 20, 1999

[54] BIS ALKANOYL ESTERS OF CARNITINE HAVING BACTERICIDAL, FUNGICIDAL AND ANTIPROTOZOAL ACTIVITY

[76] Inventors: Nazareno Scafetta, Via Siena, 10, 00040 Pavona di Albano RM; Maria Ornella Tinti, Via Ernesto Basile, 81, 00182 Rome; Francesco De Angelis, Piazza A. Friggeri, 13, 00136 Rome; Gian Carlo Gramiccioli, Via IV Novembre, 56, 00040 Ariccia RM, all of Italy

[21] Appl. No.: 08/818,737

[22] Filed: Mar. 14, 1997

[30] Foreign Application Priority Data

Mar. 20, 1996 [IT] Italy ................ RM96A0180

[51] Int. Cl.$^6$ .................................... A01N 25/00
[52] U.S. Cl. .................. 424/405; 514/529; 514/533; 514/547; 560/76; 560/190
[58] Field of Search ............ 424/405; 514/529, 514/533, 547; 560/76, 190

[56] References Cited

U.S. PATENT DOCUMENTS 2,497,673  2/1950  Kirk et al. ........................ 560/76
2,712,025  6/1955  Rehberg et al. ................... 560/76

FOREIGN PATENT DOCUMENTS 220538   5/1987  European Pat. Off. .
552137   7/1993  European Pat. Off. .
552138   7/1993  European Pat. Off. .

*Primary Examiner*—Neil S. Levy
*Attorney, Agent, or Firm*—McDonnell, Boehnen, Hulbert & Berghoff

[57] ABSTRACT

DL-, D- or L-carnitine esters of formula

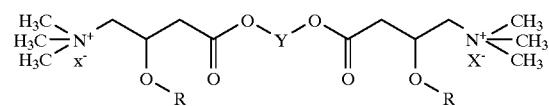

(I)

wherein R, Y and $X^-$ have the meaning shown in the specification which possess potent bactericidal, fungicidal and antiprozoal activity, processes for their preparation and compositions topically applicable for treating infections of the skin, outer ear and mucosa, are disclosed.

11 Claims, No Drawings

BIS ALKANOYL ESTERS OF CARNITINE HAVING BACTERICIDAL, FUNGICIDAL AND ANTIPROTOZOAL ACTIVITY

The present invention relates to DL-, D- or L-carnitine esters of formula (I):

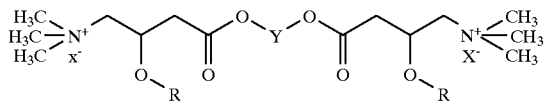

wherein:
R is a straight or branched, saturated or unsaturated alkanoyl group having 2–16 carbon atoms;
Y is a straight or branched alkylene chain having 3–6 carbon atoms, or ortho, meta or para-xylilene; and
$X^-$ is the anion of a pharmacologically acceptable acid.

The compounds of formula (I) possess two chiral centers. Each one of them can present, independently from the other one, either the D or L configuration.

The compounds of formula (I) are endowed with potent bactericidal, fungicidal and antiprotozoal activity.

The present invention also relates to processes for preparing the compounds (I) and pharmaceutical compositions for the treatment of skin diseases sustained by bacteria, yeasts, fungi or protozoa as pathogens of simple or mixed infections.

As examples of cutaneous infections that can be treated with the compositions of the present invention are those brought about by dermatophytes (Tinea corporis, Tinea cruris, Tinea capitis, Tinea pedis, Tinea barbae, Tinea unguis); by yeast-like strands such as thrush, chelitis, rhinopharyngitis, vulvovaginitis, balanoposthitis, intertrigo, pityriasis versicolor, otitis, onyxhauxis, perionyxhauxis; by bacteria such as impetigo, Staphylococcus nasal carriage, erythrasma, vaginosis; and by protozoa, such as cutaneous Leichmaniasis, keratitis sustained by Acanthamoeba, vaginitis sustained by Trichomonas.

Among the mixed cutaneous infections vulvovaginitis, vaginosis, balanitis and balanoposthitis, onychauxis and perionichauxis, infected cutaneous ulcers in patients suffering from diabetes, infections of the outer ear, and infections in immunocompromised patients should be mentioned.

The compositions of the present invention are also useful for the treatment of infectious pathologies sustained by strains resistant to the most common antimicotics and antibiotics and in the disinfection of surgically exposed tissues.

In the compounds of formula (I), R has, preferably, 9–13 carbon atoms.

R is preferably decanoyl, undecanoyl and tridecanoyl.

Y is preferably selected from trimethylene, tetramethylene, pentamethylene, hexamethylene and ortho, meta or para-xylilene.

$X^-$ is preferably selected from chloride, bromide, methanesulfonate, phosphate, acid fumarate, fumarate, acid tartrate and tartrate.

Since the compounds of formula (I) are particularly effective in the treatment of skin diseases, the preferred compositions of the present invention are dermatological preparations suitable for the topical application, such as creams, ointments, gels, lotions, solutions and the like. Suitable compositions have been found to contain from 0.5 to 2% by weight, preferably from 1 to 1.5% by weight, of one of the compounds of formula (I).

The excipients for use in the preparation of the compositions of the invention are well-known and shall be apparent to those skilled in pharmacy and pharmaceutical technology having regard to the specific composition to be prepared.

As regard the prior art, the compounds known to the applicants which are closest to the compounds of the present invention having regard to both structure and activity considerations, are the long-chain esters of acyl L-carnitine of formula:

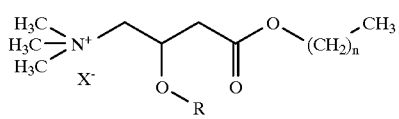

wherein R is a straight or branched acyl group having 2–16 carbon atoms; n is an integer from 7 to 15 and $X^-$ is the anion of a pharmacologically acceptable acid, disclosed in EP-A-0 552 137 and EP-A-0 552 138 both in the name of the same Applicants as those of the present patent application. EP-A-0 552 137 discloses the bactericidal activity and EP-A-O 552 138 the fungicidal activity, respectively, of such compounds.

Among these known compounds, isovaleryl L-carnitine undecyl ester methanesulfonate (compound code: ST 1103) was shown to be the most active both as bactericidal and fungicidal agent.

It has now been found that the compounds of formula (I) are endowed with bactericidal and fungicidal activity even more potent, better cutaneous tolerability and lower citotoxicity than those of the known compounds.

These compounds have also been shown to exhibit antiprotozoal activity, not previously disclosed for the known compounds.

With reference to the reaction scheme, when $A=O^-$ ($Cl^-$ is, then, missing), the process comprises the following steps:
(a) suspending an alkanoyl L-carnitine inner salt in an organic, anhydrous inert solvent such as N,N-dimethylformamide, acetonitrile or methylene chloride;
(b) adding to the suspension at 0° C.–10° C. a compound of formula Z-Y-Z wherein Y has the aforesaid meaning and Z is selected from halogen, preferably chlorine or bromine, O-mesyl or O-tosyl in an amount equivalent to one half of the moles of the alkanoyl L-carnitine;
(c) keeping the suspension under stirring at 20° C.–50° C. for 24 hours till the suspension is completely solubilized;
(d) precipitating the reaction raw product by adding a solvent such as ethyl ether or hexane, filtering off the product and washing with acetone or methylethyl ketone till a solid product is obtained;
(e) dissolving the product in water and eluting on a strongly basic resin such as Amberlite IRA-402 activated with a suitable acid of formula HX to obtain the product salified in the sought-after form;
(f) lyophilizing or concentrating the eluate for isolating the solid product; and
(g) purifying the solid of step (f) by chromatography on $C_8$ silica, eluting with $H_2O/CH_3N$ 70:30.

Alternatly, when A=Cl, the process comprises the following steps:
(a') suspending the alkanoyl L-carnitine acid chloride in an organic, anhydrous inert solvent such as N,N-dimethylformamide, acetonitrile or methylene chloride;
(b') adding to the suspension at room temperature a compound of formula Z-Y-Z wherein Y has the aforesaid meaning and Z is OH in an amount equivalent to one half of the moles of the alkanoyl L-carnitine;

(c') keeping the suspension under stirring at room temperature for 16–24 hours till the suspension is completely solubilized;
(d') concentrating the solution to dryness under vacuum;
(e') purifying the raw product thus obtained by silica gel chromatography, eluting with $H_2O/CH_3CN$ solutions; and
(f') isolating the compound by concentration and subsequent lyophilization.

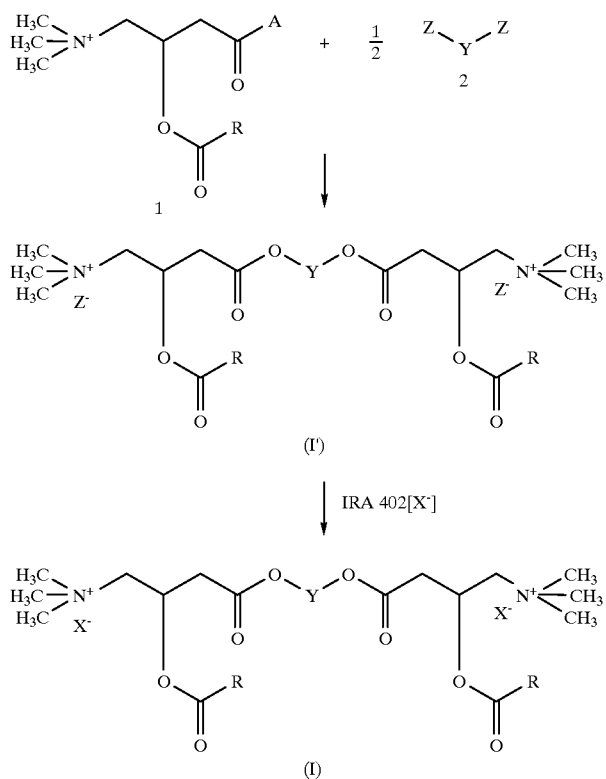

$A = O^-$, Cl
$Y$ = as previously described
$Z$ = Cl, Br, I, OMs, OTs, OH
Ms = mesyl
Ts = tosyl
$X^-$ = anion of pharmacologically acceptable acid.

The preparation and physico-chemical characteristics of some compounds of the invention are shown in the following non-limiting examples.

EXAMPLE 1

Preparation of bis(undecanoyl L-carnitine chloride)p-xylilene diester (ST 1226)

Undecanoyl L-carnitine inner salt (8.5 g; 0.025 moles) was suspended in 50 mL of anhydrous N,N-dimethylformamide.

To the suspension, cooled to 0° C., α,α'-dibromo p-xylene (3.4 g; 0.013 moles) was added. The resulting mixture was kept under stirring for 4 hours till complete solubilization was achieved. Ethyl ether was added to the solution till precipitation of a gelly mass was completed.

The raw product thus obtained was repeatedly washed with acetone and filtered under vacuum yielding 7 g of a solid product. Molar yield 65% (calculated on α, α'-dibromo p-xylene).

The product was dissolved in water and eluted on IRA-402 (140 mL) activated in Cl⁻ form.

From the lyophilized eluate, 6.3 g of a slightly hygroscopic product were obtained.

Elementary Analysis for $C_{44}H_{78}O_8N_2Cl_2$

|  | C % | H % | N % | Cl % |
|---|---|---|---|---|
| Calculated | 62.68 | 10.40 | 3.32 | 8.41 |
| Found | 60.25 | 8.98 | 3.03 | 8.10 |

$H_2O$ 1.4%

HPLC

Column: SGE-SCX (5 μm) 1 250 mm×4.0 mm temp.: 30° C.

eluant: $CH_3CN/NH_4H_2PO_4$ 50 mM 65/35 pH=7 ($NH_4OH$)

flow rate: 0.75 mL/min

Rt: 17.6 min $[\alpha]_{25}^D = -17$ (c=0.6% $H_2O$)

NMR $CDCl_3$ ¹H δ7.4(4H,s,phenyl); 5.6(2H,m,2

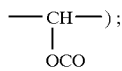

5.2(4H,s,2$CH_2$phenyl); 4.2–4.0(4H,dd,2N⁺$CH_2$); 3.4(18H,s, 2($CH_3$)₃N⁺); 3.0–2.8(4H,m,2 $CH_2$COO); 2.3(4H,t,2 OCO$CH_2$); 1.6(4H,m,2 C$\underline{H}_2$$CH_3$); 1.1(32H,m,2($CH_2$)₈); 0.9 (6H,t,2$CH_3$)

EXAMPLE 2

Preparation (via the acid chloride route, see reaction scheme, A=Cl) of Bis(undecanoyl L-carnitine chloride)p-xylilene diester (ST 1226).

Undecanoyl L-carnitine chloride (18 g; 0.05 moles) was suspended in 50 mL methylene chloride and to the resulting mixture thionyl chloride (7.5 mL; 0.1 moles) was added. The mixture was kept under stirring at room temperature for 3 hours.

The mixture was then concentrated under vacuum, the residue washed repeatedly with $Et_2O$ and concentrated.

The reaction product was suspended in anhydrous methylene chloride (50 mL) and to the mixture 1,4-benzenedimethanol was added portionwise over 2 hours. The resulting mixture was kept under stirring at room temperature overnight. The reaction mixture was concentrated under vacuum.

The reaction raw product was purified by chromatography over $C_8$ silica gel, eluting with $H_2O/CH_3CN$ 70:30.

The fractions containing the title compound (ST 1226) were concentrated and then lyophilized.

The product thus obtained showed the same characteristics as those of the compound obtained in Example 1.

EXAMPLE 3

Preparation of bis(tridecanoyl L-carnitine chloride) trimethylene diester (ST 1233)

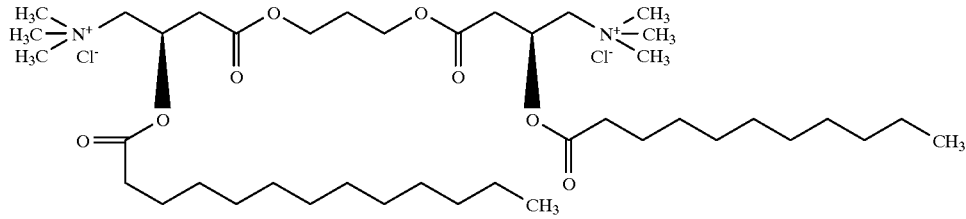

Tridecanoyl L-carnitine inner salt (5.15 g; 0.0144 moles) was suspended in 50 mL of anhydrous N,N-DMF. To the suspension, cooled to 0° C., 1,3-dibromopropane (0.73 mL; 0.0072 moles) was added. The resulting mixture was kept under stirring overnight at room temperature.

Then, an excess of tridecanoyl L-carnitine inner salt (0.5 g) was twice added and the mixture was further kept under stirring overnight till the reaction mixture was completely dissolved.

At the end of the reaction, ethyl ether was added till the reaction raw product completely precipitated.

The solid was filtered off giving 6 g of a product which was dissolved in water and eluted on IRA-402 (120 mL) activated in Cl⁻ form.

5 g of the title compound (ST 1233) were obtained. Yield 44%.

Elementary Analysis for $C_{43}H_{84}O_8N_2Cl_2$

|  | C % | H % | N % | Cl % |
|---|---|---|---|---|
| Calculated with 3.35% $H_2O$ | 60.28 | 10.25 | 3.27 | 8.27 |
| Found | 60.82 | 10.46 | 3.17 | 8.50 |

$[\alpha]_D^{25} = -13.2°$ (c=1% $H_2O$) NMR $CDCl_3$ ¹H δ5.6(2H, m,2-CHOCO); 4.5(2H,d,2N⁺—C$\underline{H}$H); 4.3–3.9(6H,m, 2N⁺—CH$\underline{H}$;2$CH_2$O); 3.5(18H,s,2($CH_3$)₃ N⁺); 3.0–2.8(4H, 2$CH_2$COO); 2.3(4H,t,OCO$CH_2$); 2.0(2H,m,—$CH_2$—$CH_2$—$CH_2$—); 1.6(4H,m,2C$\underline{H}_2$$CH_3$); 1.2(36H,s,2($CH_2$)₉); 0.8(6H,t,2$CH_3$)

EXAMPLE 4

Preparation of bis(undecanoyl L-carnitine chloride)o-xylilene diester (ST 1249)

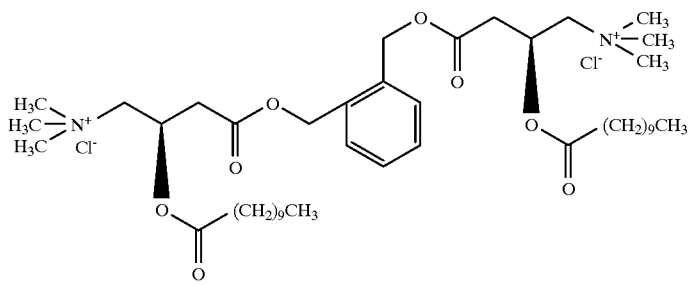

The title compound was prepared and isolated as described in Example 1. Yield 58%.

Elementary Analysis corresponding to $C_{44}H_{78}O_8N_2Cl_2$

HPLC

Column: SGE-SCX (5 μm) 1 250 mm×4.0 mm temp.: 30° C.

eluant: $CH_3CN/NH_4H_2PO_4$ 50 mM 65/35 pH=7.2 ($NH_4OH$)

flow rate: 1 mL/min

Rt: 9.68 min $[\alpha]_D^{25}=-16°$ (c=1% $H_2O$)

NMR corresponding, as in Example 1.

EXAMPLE 5

Preparation of bis-(undecanoyl-L-carnitine chloride)m-xylilene diester (ST 1250)

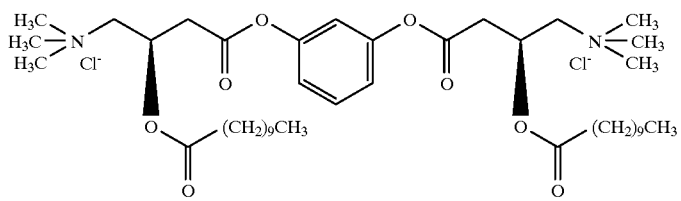

The title compound was prepared and isolated as described in Example 1. Yield 78%.

Elementary Analysis corresponding to $C_{44}H_{78}O_8N_2Cl_2$

HPLC as described in Example 1

Rt=9.18 min

NMR corresponding, as described in Example 1

$[\alpha]^{25}=-18.2°$ (c=0.5% $H_2O$)

The potent bactericidal, fungicidal and antiprotozoal activity of the compounds of the present invention and their superiority to the closest prior art compounds, such as the above-mentioned isovaleryl L-carnitine undecyl ester methanesulfonate (ST 1103) was assessed in several pharmacological tests, some of which are hereinbelow described.

IN VITRO ANTIMICROBIAL ACTIVITY

Minimal Inhibitory Concentration (mcg/ml) of ST1226 in Comparison with ST 1103 on Gram Positive and Gram Negative Bacteria (Lab Collection and Fresh Clinical Isolates of Dermatalogical Interest)

Material and Methods

Bacterial suspensions are prepared from an overnight culture in Mueller-Hinton broth and are adjusted, in the same medium, to a final concentration of $5.0×10^4$ cells/ml in each well of a 96-well microtiter plate. Substance dilutions (0.3 log) in Mueller-Hinton broth are added to the suspensions in order to have a range of final concentrations from 0.19 to 100 mcg/ml.

Microtiters are then incubated at 37° C. for 18 hours. (See L. D. THRUPP, Susceptibility testing of antibiotics in liquid media, in: *Antibiotics in laboratory medicine*. V. LORIAN Ed., II edition, 4, 93–150, Williams & Wilkins, Baltimora, Md. 21202 U.S.A.).

Results

The data concerning the strains of lab collection and clinical isolates are reported in tables 1 and 2, respectively. As it can be seen from both single results and from mean MIC values, ST 1226 exhibits a higher activity than ST 1103 on Gram positive bacteria (Tab. 1a and 1b).

On the contrary, no significant differences have been found between the two substances on Gram negative bacteria (Table 2a and 2b).

TABLE 1A

Minimal Inhibitory Concentration (mcg/ml) of ST 1226 and ST 1103 against Gram positive bacteria (lab collection).

| Microbial strains | ST 1226 | ST 1103 |
|---|---|---|
| Gram + | | |
| *B. pumilus* CN 607 | 1.56 | 3.12 |
| *S. faecalis* 509 | 1.56 | 1.56 |
| *S. faecalis* 501 | 3.12 | 3.12 |
| *S. aureus* 306 MR | 3.12 | 6.25 |
| *S. aureus* 303 | 3.12 | 6.25 |
| Mean MIC | 2.49 | 4.06 |

TABLE 1B

Minimal Inhibitory Concentration (mcg/ml) of ST 1226 and ST 1103 against Gram positive bacteria (clinical isolates)[a]. The diagnosis of the cutaneous infection from which the bacterial strains were isolated is indicated only when it was known.

| Microbial strains | ST 1226 | ST 1103 | Diagnosis |
|---|---|---|---|
| Staph. sp. SG1 II | 3.12 | 6.25 | — |
| Staph. aureus IDI 3530 | 3.12 | 3.12 | ulcer |
| Staph. aureus IDI 3593 | 3.12 | 3.12 | ulcer |
| Staph. aureus SG II | 3.12 | 3.12 | — |
| Staph. epider. IDI 3482 | 3.12 | 1.56 | suppurative wound |
| Staph. capitis IDI 3502 | 1.56 | 3.12 | pustule (scalp) |
| Staph. warneri IDI 3482 | 3.12 | 6.25 | suppurative wound |
| Strept. faecalis IDI 3580 | 6.25 | 6.25 | ulcer |
| Strept. sp. SG 7 II | 3.12 | 3.12 | — |
| Micrococcus sp. IDI 3502 | 1.56 | 3.12 | pustule (scalp) |
| Mean MIC | 3.12 | 3.90 | |

[a]SG strains (from S. Gallicano Hospital of Rome). IDI strains (from Immacolata Dermatological Institute of Rome).

TABLE 2A

Minimal Inhibitory Concentration (mcg/ml) of ST 1226 and ST 1103 against Gram negative bacteria (lab collection).

| Microbial strains | ST 1226 | ST 1103 |
|---|---|---|
| Gram – | | |
| S. typhimurium DS | 25 | 25 |
| E. aerogenes UM | 6.25 | 25 |
| P. vulgaris UM | 50 | 50 |
| K. oxytoca 552 | 25 | 12.5 |
| E. coli 92 F | 25 | 25 |
| Mean MIC | 26.25 | 27.5 |

TABLE 2B

Minimal Inhibitory Concentration (mcg/ml) of ST 1226 and ST 1103 against Gram negative bacteria (clinical Isolates)[a]. The diagnosis of the cutaneous infection from which the bacterial strains were isolated is indicated only when it was known.

| Microbial strains | ST 1226 | ST 1103 | Diagnosis |
|---|---|---|---|
| Pseudomonas aeruginosa IDI 3530 | 50 | 25 | ulcer |
| Klebsiella pneumoniae SG 5 II | 50 | 50 | — |
| Enterobacter cloacae SG 3 II | 12.5 | 25 | — |
| Escherichia coli SG 4 II | 12.5 | 25 | — |
| Proteus sp. SG 9 II | 50 | 50 | — |
| Mean MIC | 35.0 | 35.0 | |

[a]SG strains (from S. Gallicano Hospital of Rome). IDI strains (from Immacolata Dermatological Institute of Rome).

Minimal Inhibitory Concentration (mcg/ml) of ST 1226 in Comparison with ST 1103 on Gram Positive and Gram Negative Anaerobic Bacteria (Lab Collection and Clinical Isolates)

Materials and Methods

Bacteria from cultures in WILKINS-CHALGREN (W. C.) medium on Petri dishes, grown overnight at 35° C. in an anaerobic jar, were resuspended in Brucella broth. The suspensions were adjusted to $1.0 \times 10^8$ cells/ml and distributed (0.2 ml/well) in microtiter plates (96-well U-bottomed plate). At the same time, 0.3 log dilutions of the substances are mixed with W. C. agar medium in four-sectioned Petri dishes, which are then seeded with the bacterial suspension by means of a multipoint inoculator ($1.0 \times 10^5$ cells/spot). The plates are then incubated at 35° C. for 48 hours in an anaerobic jar) (See J. E. ROSENBLATT, Antimicrobial susceptibility testing of anaerobes, in Antibiotics in laboratory medicine. V. LORIAN Ed., II edition, 6, 159–180, Williams & Wilkins, Baltimora, Md 21202 U.S.A.).

Results

The MIC values (mcg/ml) of the compounds against 3 anaerobic bacterial strains are reported in Table 3. The mean MIC value of ST 1226 is smaller than ST 1103.

TABLE 3

Minimal Inhibitory Concentration (mcg/ml) of ST 1226 and ST 1103 against anaerobic bacteria. The diagnosis of the cutaneous infection from which the bacterial strains were isolated is indicated only when it was known.

| Microbial strains | ST 1226 | ST 1103 | Diagnosis |
|---|---|---|---|
| Eubacterium lentum IDI 3502* | 6.25 | 3.12 | suppurative wound |
| Propionibacterium acnes IDI 3482* | 6.25 | 6.25 | suppurative acne |
| Bacteroides fragilis ATCC 25285** | 12.5 | 25 | — |
| Mean MIC | 8.33 | 11.45 | |

*Gram positive bacteria (clinical isolates from Immacolata Dermatological Institute of Rome).
**Gram negative bacterium (lab collection).

Minimal Inhibitory Concentration (mcg/ml) of ST 1226 in Comparison with ST 1103 on Yeast-Like Strains (Lab Collection and Clinical Isolates)

Materials and Methods

Overnight yeast cultures in Sabouraud broth are appropriately washed and diluted in Yeast Nitrogen Base supplemented with asparagine and glucose (Y.N.B.s.) to yield approximately $5.0 \times 10^4$ CFU/ml in microtiter wells. Substance dilutions (0.3 log) in Y.N.B.s. are added to these suspensions to a final concentration range from 0.19 to 100 mcg/ml. Microtiter plates are then incubated at 35° C. for 24–48 hours (See PFALLER M., RINALDI M. G., GALGIANI J. M., BARTLETT M. S., BODY B. A., ESPINEL-INGROFF A., FROMTLING R. A., HALL G. S., HUGHES G. E., ODDS F. C., SUGAR A. M., Collaborative investigator of variables in susceptibility testing of yeasts, Ant. Agent and Chemoth., 34, 9:1648–1656, 1990. COOK R., McINTYRE K. A., GALGIANI J. M., Effects of incubation temperature, inoculum size, and medium on agreement of macro and microdilution broth susceptibility test, results for yeasts, Ant. Agent and Chemoth., 34, 8:1542–1545, 1990. ANAISSIE E., PAETZNICK V., BODEY G. P., Fluconazole susceptibility testing of "Candida albicans" microtiter method that is indipendent of inoculum size, temperature, and time of reaching, Ant. Agent and Chemoth., 35, 8:1641–1646, 1991).

Results

The data concerning the lab collection strains and the clinical isolates are reported in tables 4 and 5, respectively. ST 1226 exhibits a higher activity than ST 1103, mostly against Candida clinical isolates of dermatological interest.

TABLE 4

Minimal Inhibitory Concentration (mcg/ml) of ST 1226 and ST 1103 against yeast-like strains (lab collection).

| Microbial strains | ST 1226 | ST 1103 |
|---|---|---|
| S. cerevisiae ATCC 7752 | 1.56 | 3.12 |
| C. krusei ISS 1 | 3.12 | 3.12 |
| C. tropicalis ISS 1 | 1.56 | 3.12 |
| C. albicans ISS 1 | 3.12 | 1.56 |
| C. albicans 562 | 3.12 | 3.12 |
| Mean MIC | 2.49 | 2.80 |

TABLE 5

Minimal Inhibitory Concentration (mcg/ml) of ST 1226 and ST 1103 against Candida strains (clinical isolates)[a]. The diagnosis of the cutaneous infection from which the Candida strains were isolated is indicated only when it was known.

| Microbial strains | ST 1226 | ST 1103 | Diagnosis | Treatment[b] |
|---|---|---|---|---|
| Candida albicans SG 14 III | 1.56 | 6.25 | Vaginitis | — |
| Candida albicans SG 7 I | 3.12 | 3.12 | Tinea unguis (hands) | — |
| Candida albicans IDI D 3575 | 3.12 | 6.25 | — | — |
| Candida albicans IDI D 0297 | 3.12 | 3.12 | Vulvar vaginitis | Pevaryl ® |
| Candida aibicans IDI D 1088 | 3.12 | 3.12 | — | — |
| Candida albicans IDI D 0101 | 1.56 | 6.25 | Eczema (internatal) | Versus ® |
| Candida albicans IDI D 1056 | 1.56 | 3.12 | — | — |
| Candida albicans SG 2 III | 1.56 | 6.25 | Vaginitis | — |
| Candida albicans 1786/94 | 3.12 | 6.25 | — | — |
| Candida albicans IDI D 1046 | 3.12 | 3.12 | Glossitis | Daktarin ® |
| Mean MIC | 2.49 | 4.68 | | |

[a]SG strains (from S. Gallicano Hospital of Rome). IDI strains (from Immacolata Dermatological Institute of Rome). SM strains (from S. Matteo Hospital of Pavia).
[b]Treatment administered prior to clinical diagnosis.

Minimal Inhibitory Concentration (mcg/ml) of ST 1226 in Comparison with ST 1103 on Filamentous Fungi (Lab Collection)

Materials and Methods

The conidia are collected from 72-hour cultures in Sabouraud agar by washing them with Sabouraud broth and 0.5% Tween 80. After a coarse filtration and washing, the resulting suspensions are adjusted to a final concentration of approx. $5.0 \times 10^4$ CFU/ml in a microtiter plate. The substances (0.3 log dilutions in Y.N.B.s.) are added to the fungal suspensions in order to generate a range of final concentrations from 0.19 to 100 mcg/ml. The microtiter plates are then incubated at 35° C. for 48–72 hours.

Results

The results obtained with the two compounds are shown in table 6. Both single results and mean MIC values clearly show that ST 1226 exhibits a markedly higher activity than ST 1103.

TABLE 6

Minimal Inhibitory Concentration (mcg/ml) of ST 1226 and ST 1103 against filamentous fungi (lab collection).

| Microbial strains | ST 1226 | ST 1103 |
|---|---|---|
| Fusarium sp. F 77 | 3.12 | 6.25 |
| Penicillium sp. 1302 | 1.56 | 12.5 |
| Mucor mucedo ATCC 7941 | 25 | 50 |
| Aspergillus niger ATCC 16404 | 6.25 | 12.5 |
| Aspergillus fumigatus ATCC 28212 | 6.25 | 12.5 |
| Mean MIC | 8.43 | 18.75 |

Minimal Inhibitory Concentration (mcg/ml) of ST 1226 in Comparison with ST 1103 on Dermatophytes (Clinical Isolates of Dermatological Interest)

Materials and Methods

Mycelium fragments, micro and macroaleuriospores are harvested from 7-day fungal cultures grown at 30 ° C. in Potato Dextrose agar by washing them with Sabouraud broth and 0.5% Tween 80. After a coarse filtration and washing, the fungal suspension is resuspended in Yeast Nitrogen Base supplemented with asparagine and glucose (YNBs) to yield a final concentration of $1.0 \times 10^5$ infective units/ml in a microtiter plate.

The substances (0.3 log dilutions in Y.N.B.s.) are added to the fungal suspensions in order to generate a range of final concentrations from 0.19 to 100 mcg/ml. The microtiter plates are then incubated at 30° C. for 96–120 hours.

Results

The results obtained with the two compounds are reported in table 7. It can be easily seen that ST 1226 displays a higher activity than ST 1103 against dermatophytes.

TABLE 7

Minimal Inhibitory Concentration (mcg/ml) of ST 1226 and ST 1103 against dermatophytes (clinical isolates)[a]. The diagnosis of the cutaneous infection from which the bacterial strains were isolated is indicated only when it was known.

| Microbial strains | ST 1226 | ST 1103 | Diagnosis | Treatment[b] |
|---|---|---|---|---|
| Tr. mentagrophytes IDI D 1101 | 1.56 | 12.5 | Epidermatomycosis (face) | — |
| Tr. mentagrophytes SG 8 II | 1.56 | 12.5 | Tinea cruris | — |
| Tr. mentagrophytes SG 3 I | 1.56 | 12.5 | Tlnea pedis | — |
| Tr. mentogrophytes SG 4 II | 1.56 | 12.5 | Tinea cruris | — |
| Tr. mentagrophytes SG 5 III | 3.12 | 12.5 | Tinea pedis | — |
| Tr. mentagrophytes IDI D 1027 | 3.12 | 12.5 | Impetiginous eczema (chin) | — |
| Tr. mentagrophytes IDI D 1049 | 1.56 | 12.5 | — | — |
| Tr. quinckeanum NCPF 309* | 1.56 | 6.25 | — | — |
| Tr. rubrum IDI D 0222 | 1.56 | 12.5 | Onychomycosis (left and right big toes) | — |
| Tr. rubrum IDI D 0261 | 1.56 | 12.5 | Dyshidrotic eczema (right foot) | Fargan ® Gentalyn β ® and cortisone |
| Tr. rubrum SG 13 III | 1.56 | 12.5 | Tinea pedis | — |
| Tr. rubrum IDI D 1017 | 1.56 | 12.5 | Onychomycosis (right big toe) | Azolmen ® |
| Tr. rubrum | 1.56 | 25 | Impetigo (left arm) | Rifocin ® |

TABLE 7-continued

Minimal Inhibitory Concentration (mcg/ml) of ST 1226 and ST 1103 against dermatophytes (clinical isolates)[a]. The diagnosis of the cutaneous infection from which the bacterial strains were isolated is indicated only when it was known.

| Microbial strains | ST 1226 | ST 1103 | Diagnosis | Treatment[b] |
|---|---|---|---|---|
| IDI D 0252 | | | | |
| Tr. rubrum IDI D 1150 | 1.56 | 12.5 | Epidermophytosis (arms, legs and buttocks) | Gentalyn ® |
| Tr. rubrum IDI D 1155 | 1.56 | 3.12 | — | — |
| Microsporum canis IDI D 1123 | 1.56 | 12.5 | Epidermophytosis (back) | Gentalyn ® |
| Microsporum canis IDI D 0238 | 12.5 | 25 | Tricophytosis (right arm) | Nerisona ® |
| Microsporum canis IDI D 1011 | 3.12 | 12.5 | Eczema (neck) | Gentalyn ® and cortisone |
| Microsporum canis IMM 3868* | 1.56 | 12.5 | — | — |
| Epidermoph. floccosum IDI D 0011 | 12.5 | 12.5 | Epidermophytosis (foot interdigital) | — |
| Epidermoph. floccosum SG 6 II | 6.25 | 12.5 | Tinea pedis | — |
| Epidermoph. floccosum SG 3 III | 6.25 | 25 | — | — |
| Mean MIC | 3.19 | 13.49 | | |

*lab collection strains.
[a]SG strains (from S. Gallicano Hospital of Rome). IDI strains (from Immacolata Dermatological Institute of Rome).
[b]Treatment administered prior to clinical diagnosis.

Minimal Inhibitory Concentration (mcg/ml) of ST 1226 in Comparison with ST 1103 on Protozoa (*Trichomonas vaginalis*)

Materials and Methods

Protozoal suspensions are prepared from 24-hour cultures grown at 37° C. and 5% $CO_2$ in DIAMOND T.Y.M. broth supplemented with 10% heat-inactivated FCS.

The suspensions are adjusted, in the same medium, to a final concentration of $2.5 \times 10^5$ cells/ml in each well of a 96-well microtiter plate. Substance dilutions (0.3 log) are added to the suspensions in order to have a range of final concentrations from 0.19 to 100 mcg/ml. Microtiters are then incubated at 37° C. and 5% $CO_2$ for 24 hours. MIC is referred to as the minimal concentration inhibiting either protozoa or flagella or undulating membrane motility (Cf. JULIANO C., MARTINOTTI M. G., CAPPUCCINELLI P., In vitro effect of microtubule inhibitors on *T. vaginalis, Microbiologia*, 8:31–42, 1985. LÖVGREN T. and SALMELA I., Invitro sensitivity of T. vaginalis and C. albicans to chemotherapeutic agents, *Acta Path. Microbiol. Scand.*. 86:155–158, 1978).

Results

The results obtained with the two substances are shown in table 8: ST 1226 exhibits a greater (2-fold) activity than ST 1103.

TABLE 8

Minimal Inhibitory Concentration (mcg/ml) of ST 1226 and ST 1103 against *T. vaginalis* strains[a].

| Microbial strains | ST 1226 | ST 1103 |
|---|---|---|
| T. vaginalis SS-2 | 12.5 | 25 |
| T. vaginalis SS-9 | 12.5 | 25 |
| T. vaginalis SS-20[b] | 12.5 | 25 |
| T. vaginalis SS-22[b] | 12.5 | 25 |
| Mean MIC | 12.5 | 25 |

[a]Strains from the Institute of Microbiology and Virology of the Univerisity of Sassari.
[b]Strains Metronidazole-resistant (MIC of 25 and 50 mcg/ml).

IN VIVO ACTIVITY

Evaluation of the In Vivo Antiinfective Effect of ST 1226 and 1103 on Topical Mixed Infection Sustained by a Dermatophyte (*Tricophyton quinckeanum*) and by a Gram Positive Bacterium (*Staphylococcus aureus*)

Materials and Methods

Animals

Male inbred BALB/c mice (C. RIVER), aged 6 weeks were used (5 animals per group).

Microbial strains

The animals were topically infected with pathogenic strains of Tricophyton (*Tricophyton quinckeanum* NCPF 309) and Staphylococcus (*Staphylococcus aureus* LC1).

Experimental procedure

Suspensions of fungal microaleuriospores and bacteria were adjusted to a final concentration of $5.0 \times 10^7$ and $1.0 \times 10^7$ cells/ml, respectively. Volumes of 0.2 ml of each suspension were applied onto the upper posterior zone of the animals, which had previously been shaved and gently abraded with a scalpel blade until "glistening". Treatment started 30 hours after the inocula by administering 50 mg of each substance in a gel form (1% test article) on the infected skin once a day for 5 consecutive days. Two days following the last treatment, animals were sacrificed and infected tissue samples were collected. Following homogenization and appropriate dilution in medium, tissue samples were plated (in Mycobiotic agar and Mannitol Salt agar for fungi and bacteria, respectively) to selectively assess the growth of the pathogens. Fungal growth is evaluated by means of an arbitrary scale, while bacterial growth is evaluated by determining the CFUs (Colony Forming Units).

Results

The results obtained with both molecules are shown in Table 9. It can be inferred that the molecules have both an identical activity on *S. aureus*, while ST 1226 exhibits a greater antinfungal activity than ST 1103.

TABLE 9

In vivo antiinfective efficacy of ST 1226 in comparison with ST 1103 on a mixed topical infection (*Tricophyton quinckeanum* NCPF 309 and *Staphylococcus aureus* LC1) in mice[a].

| | S. aureus | | T. quinckeanum | |
|---|---|---|---|---|
| Treatment | Cured animals (%) | Not cured animals (mean CFU/mouse) | Cured animals (%) | Not cured animals (fungal growth)[c] |
| Control | 0 | $2.73 \times 10^4$ | 0 | ++ |
| Vehicle | 0 | $3.36 \times 10^4$ | 0 | ++/+ |

TABLE 9-continued

In vivo antiinfective efficacy of ST 1226 in comparison with ST 1103 on a mixed topical infection (*Tricophyton quinckeanum* NCPF 309 and *Staphylococcus aureus* LC1) in mice[a].

| | S. aureus | | T. quinckeanum | |
|---|---|---|---|---|
| Treatment | Cured animals (%) | Not cured animals (mean CFU/mouse) | Cured animals (%) | Not cured animals (fungal growth)[c] |
| ST 1103[b] | 80 | 40 | 80 | + |
| ST 1226[b] | 80 | 50 | 100 | — |

[a] 5 animals per experimental group.
[b] Animals were topically treated for 5 consecutive days by administering 50 mg/day of each substance at 1% in gel (Hydroxyethyl-cellulose, 2.5 gr.; Glycerin, 7.0 gr.: Propylene Glycol, 7.0 gr.: depurated water up to 100 ml).
[c] +++ confluent fungal growth (from a 1-ml skin homogenate)
++ semiconfluent fungal growth (from a 1-ml skin homogenate)
+ moderate fungal growth (from a 1-ml skin homogenate).

Evaluation of Dermal Tolerability After Repeated Treatments (10 Days) with ST 1226 and ST 1103 on Mouse Scarified Skin Materials and Methods Animals Male CD1 mice (C. RIVER), aged 6 weeks, were used (5 animals per group).

Substances

Substance formulations (1% of test article) were prepared in gel (Hydroxyethyl-cellulose, 2.5 gr.; Glycerin, 7.0 gr.; Propylene Glycol, 7.0 gr.; water up to 100 ml).

Experimental procedure

The central dorsal zone of the animals was first shaved, and then gently abraded with a scalpel blade. Treatment was performed 1 day following the dermal abrasion by administering 50 mg of each substance formulation once a day, for 10 consecutive days. The treated skin areas were examined at 5, 7, 9, and 11 days following scarification. The evaluation was based upon grading of the lesions as ERYTHEMA (E), DESQUAMATION (D), and CRACKING (C), according to the following scale:

| E | D | C |
|---|---|---|
| 0 = no erythema | 0 = none | 0 = none |
| 1 = slight (barely visible) | 1 = slight (barely visible) | 1 = slight (cracks in epidermis) |
| 2 = moderate (well defined) | 2 = moderate (scabs and scales) | 2 = moderate (cracks in dermis) |
| 3 = severe (purplish red) | 3 = pronounced (scales with denuded areas) | 3 = pronounced (cracks with bleeding) |

The mean of the values of each parameter in the same animal group allowed us to evaluate the tissue damage provoked by the substance under examination.

Results

The results obtained with the compounds, expressed as the mean of each parameter evaluated in the same experimental group, are reported in Table 10. It can be seen that ST 1226 is better tolerated than ST1103.

TABLE 10

Dermal tolerability of repeated administrations of St 1226 and ST 1103 on murine scarified skin. Evaluation on days 5, 7, 9, and 11 following scarification by means of an arbitrary scale (erythema, desquamation, and cracking) ranging from 0 (no effect) to 3 (severe damage). The results are expressed as mean values of each experimental group (5 animals/group).

| | +5[a] | | | +7[a] | | | +9[a] | | | +11[a] | | |
|---|---|---|---|---|---|---|---|---|---|---|---|---|
| Treatment | E | D | C | E | D | C | E | D | C | E | D | C |
| Control | 0.2 | 0 | 0 | 0 | 0 | 0 | 0 | 0 | 0 | 0 | 0 | 0 |
| Vehicle | 0.2 | 0 | 0 | 0 | 0 | 0 | 0 | 0 | 0 | 0 | 0 | 0 |
| ST 1103 | 1.2 | 0.4 | 0 | 0.4 | 0.4 | 0 | 0 | 0 | 0 | 0 | 0 | 0 |
| ST 1226 | 0.2 | 0 | 0 | 0 | 0 | 0 | 0 | 0 | 0 | 0 | 0 | 0 |

[a] = days following dermal scarification.

Evaluation of the Antifungal Activity of ST 1226 (1% and 1.5%) and Miconazole (1.5%) in an Experimental Infection Model (Tinea pedis) Induced in the Paw of the Guinea-Pig with a Strain of Trichophyton (*T. mentagrophytes* IDI D1049)

The characteristics of chronic infection and the similarity with the human infection, from an histological and clinical standpoint, make this model very useful to study the most wide-spread topical fungal pathology (athlete's foot). Besides, the outcome of the treatment may constitute a good point of reference from which one can extrapolate valuable indications on other dermatophytes infecting different body areas. Moreover, the chronicity of this infection (up to 6 months) allows the substances to be studied even with long-lasting treatments, as it usually happens in man.

In the present investigation, we have evaluated in the guinea-pig model whether ST 1226, at two different concentrations, was able to cure this typical cutaneous dermatophytic infection, which is long-lasting and of frequent occurrence in man.

Materials and Methods

Animals

Twelve male Hartley guinea-pig (C. RIVER), weighing 350–400 gr, have been utilized (3 animals per experimental group).

Infective strain

One clinical isolate (*Tricophyton mentagrophytes* IDI D 1049, from Immacolata Dermatological Institute of Rome) was utilized.

Inoculum preparation

Microaleuriospores were first harvested by scraping from a 7-day fungal culture grown in Potato dextrose agar, and then resuspended in Sabouraud broth with 0.5% Tween 80. After washing, the spores were standardized in sterile saline to yield a final concentration of $1.0 \times 10^8$ spores/ml.

Experimental group

Five experimental groups were set up as follows:

Control I: infected animals

Control II: infected and placebo-treated animals
Treated I: infected and 1% ST 1226-treated animals
Treated II: infected and 1.5% ST 1226-treated animals
Treated III: infected and 1.5% Miconazole-treated animals.

Each group included 3 animals, and only the left hind paw was inoculated. For the 2 control groups, 3 animals in total were used, as both hind paws of each animal were inoculated.

Experimental procedure

Filter paper discs (12-mm diameter and 0.3-mm thickness) were covered with aluminum foil in the lower part to prevent the inoculum spreading. This filter was then sticked to a 1×3-cm piece of biadesive plaster, which adhered to a gauze wrapped around the paw.

The filter paper disc was then wetted with 100 µl of the infective suspension, and subsequently fixed to the guinea-pig paw.

The animal paw was tied up with bandage and plaster, and then left in these conditions for 7 days.

Seven days after infection, the infected areas were uncovered and the type of lesion was graded according to an arbitrary scale, as follows:

| ERYTHEMA | EROSION | DESQUAMATION |
|---|---|---|
| 0 = none | 0 = none | 0 = none |
| 1 = slight | 1 = slight | 1 = slight |
| 2 = moderate | 2 = moderate | 2 = moderate |
| 3 = severe | 3 = severe | 3 = severe |

These "clinical" signs were examined again on days +14, +21, and +31 (day of sacrifice of animals). Three days following the first observation of the type of lesion (day +10), treatments with the differrent formulations were started, and they went on for 20 days (once a day). Two days following the last treatment (day +31), animals were sacrificed and plantar areas of the paws were dissected into 10 parts for each paw.

These sections were plated onto Mycobiotic agar supplemented with Penicillin G and Streptomicin (100 mcg/ml). Volumes of 50 µl of both antibiotics were then added to the plantar sections to prevent any bacterial growth that might interfere with the growth of T. mentagrophytes in the samples under examination.

The data obtained were expressed as the number of microbiologically sterile cutaneous sections over the total examined sections.

Results

The results obtained with ST 1226 in this experimental model were favourable in terms of "microbiological recovery" (80% and 100% with 1% and 1.5% ST 1226, respectively) (Tab 11).

Treatment with Miconazole (1.5%) was similarly capable of eradicating infection from all treated samples.

TABLE 11

Clinical and microbiological evaluation of a cutaneous treatment with ST 1226 and Miconazole in a guinea-pig plantar infection by a strain of Trichophyton (T. mentagrophytes IDI D1049)

| Treatment | 7$^{th}$ day | | | 14$^{th}$ day$^a$ | | | 21$^{st}$ days | | | 31$^{st}$ day$^a$ | | | sterile samples (n = 30) (%) |
|---|---|---|---|---|---|---|---|---|---|---|---|---|---|
| | A | E | D | A | E | D | A | E | D | A | E | D | |
| Control I | 0 | 0 | 0 | 0 | 0.3 | 0 | 0 | 0.3 | 0.3 | 0.3 | 0.6 | 0.6 | 1/30(3.33) |
| Control II$^b$ | 0 | 0 | 0 | 0 | 0.3 | 0 | 0 | 0.3 | 0 | 0.3 | 0.6 | 0.6 | 0/30(0) |
| ST 1226 (1%) | 0 | 0 | 0 | 0 | 0 | 0 | 0 | 0 | 0 | 0 | 0 | 0 | 24/30(80) |
| ST 1226 (1.5%) | 0 | 0 | 0 | 0 | 0 | 0 | 0 | 0 | 0 | 0 | 0 | 0 | 20/20(100) |
| MCZ (1.5%) | 0 | 0 | 0 | 0 | 0 | 0 | 0 | 0 | 0 | 0 | 0 | 0 | 30/30(100) |

$^a$ = days following the infective inoculum.
$^b$ = infected animals treated with placebo (Hydroxyethyl-cellulose, 2.5 gr.; Glycerin, 7.0 gr.; Propylene Glycol, 7.0 gr.; depurated water up to 100 ml).

Comparative Evaluation of Dermal Tolerability of 4 Acqueous Formulations Containing 1% ST 1226 on Mouse Scarified Skin Materials and Methods Animals Forty-five male CD1 mice (C. RIVER), aged 7 weeks, were used (5 animals per experimental group).

Substance formulations

| Components | % |
|---|---|
| Cream TF 24/6327 | |
| ST 1226 | 1 |
| Para combin | 0.25 |
| Propylene Glicol | 2 |
| Sepigel 305 | 5 |
| Vaseline oil | 10 |
| H$_2$O to | 100 |
| Cream TF 25/6327 | |
| ST 1226 | 1 |
| Fattylan | 16 |
| Glycerin | 3 |
| Propylene glycol | 5 |
| Nipa sept. | 0.2 |
| H$_2$O to | 100 |
| Cream TF 28/6327 | |
| ST 1226 | 1 |
| Fattylan | 11.5 |
| Tween 80 | 0.3 |
| BHA | 0.004 |
| Sorbic acid | 0.2 |
| EDTA | 0.1 |
| Vaseline | 12 |
| Propylene glycol | 2.5 |
| Silicon oil | |
| AK 350 | 0.1 |

-continued

| Components | % |
|---|---|
| Vaseline oil | 5 |
| H₂O to | 100 |
| Cream TF 14/6327 | |
| ST 1226 | 1 |
| Hydroxyethyl cellulose | 1.6 |
| Glycerin | 8 |
| Propylene Glicol | 3 |
| Ethanol | 15 |
| Perfume | 0.050 |
| H₂O to | 100 |

Experimental procedure

The central dorsal zone of the animals was first shaved, and then gently abraded with a scalpel blade.

Treatment started 1 day following the dermal abrasion by administering 50 mg of each substance formulation once a day for 10 consecutive days. The treated skin areas were clinically examined 5, 7, 9, and 13 days following scarification. The evaluation was based upon grading of the lesions as ERYTHEMA (E), DESQUAMATION (D), and CRACKING (C) according to the following scale:

| E | D | C |
|---|---|---|
| 0 = no erythema | 0 = none | 0 = none |
| 1 = slight (barely visible) | 1 = slight (barely visible) | 1 = slight (cracks in epidermis) |
| 2 = moderate (well defined) | 2 = moderate (scabs and scales) | 2 = moderate (cracks in dermis) |
| 3 = severe (purplish red) | 3 = pronounced (scales with denuded areas) | 3 = pronounced (cracks with bleeding) |

The mean of the values of each parameter in the same animal group allowed us to evaluate the tissue damage provoked by the substance under examination.

Results

All placebos appear to be very well tolerated. On the contrary, among the 1% ST 1226 acqueous creams, only TF 24/6327 and TF 14/6327 are completetely safe, while both TF 25/6327, to a lesser extent, and TF 28/6327, to a greater extent, result to be badly tolerated (Table 12).

TABLE 12

Evaluation of dermal tolerability after repeated topical treatments with ST 1226 1% in 4 different vehicles on mouse scarified skin (50 mg/mouse for 10 consecutive days).

| | Days following the scarification | | | | | | | | | | | |
|---|---|---|---|---|---|---|---|---|---|---|---|---|
| | +5 | | | 7 | | | +9 | | | +13 | | |
| Treatment | E | D | C | E | D | C | E | D | C | E | D | C |
| Control | 0 | 0 | 0 | 0 | 0 | 0 | 0 | 0 | 0 | 0 | 0 | 0 |
| TF 19/6327 (P) | 0 | 0 | 0 | 0 | 0 | 0 | 0 | 0 | 0 | 0 | 0 | 0 |
| TF 24/6327 (F) | 0 | 0 | 0 | 0 | 0 | 0 | 0 | 0 | 0 | 0 | 0 | 0 |
| TF 20/6327 (P) | 0 | 0 | 0 | 0 | 0 | 0 | 0 | 0 | 0 | 0 | 0 | 0 |
| TF 25/6327 (F) | 0.4 | 0 | 0 | 0 | 0.4 | 0 | 0 | 0 | 0 | 0 | 0 | 0 |
| TF 27/6327 (P) | 0 | 0 | 0 | 0 | 0 | 0 | 0 | 0 | 0 | 0 | 0 | 0 |
| TF 28/6327 (F) | 1.0 | 0.6 | 0 | 1.0 | 1.2 | 0 | 0 | 0.2 | 0 | 0 | 0 | 0 |
| TF 12/6327 (P) | 0 | 0 | 0 | 0 | 0 | 0 | 0 | 0 | 6 | 0 | 0 | 0 |
| TF 14/6327 (F) | 0.2 | 0 | 0 | 0 | 0 | 0 | 0 | 0 | 0 | 0 | 0 | 0 |

E = Erythema; D = Desquamation: C = craking P = Placebo; F = Complete formulation (placebo + 1% ST 1226).

We claim:

1. A DL-, D- or L-carnitine ester of formula (I)

$$\text{(I)}$$

wherein:
R is a straight or branched, saturated or unsaturated alkanoyl group having 2–16 carbon atoms;
Y is a straight or branched alkylene chain having 3–6 carbon atoms, or ortho, meta or para-xylilene; and
X⁻ is the anion of a pharmacologically acceptable acid.

2. The ester of claim 1, wherein R is an alkanoyl group having 9–13 carbon atoms.

3. The ester of claim 1, wherein Y is selected from trimethylene, tetramethylene, pentamethylene and hexamethylene.

4. The ester of claim 1, wherein X⁻ is selected from chloride, bromide, methanesulfonate, phosphate, acid fumarate, fumarate, acid tartrate and tartrate.

5. An ester of claim 1, selected from the group consisting of bis(undecanoyl-L-carnitine chloride)p-xylilene diester, bis(tridecanoyl-L-carnitine chloride)trimethyl diester, bis (undecanoyl-L-carnitine chloride)o-xylilene diester, bis (undecanoyl-L-carnitine chloride)m-xylilene diester, bis (undecanoyl-D-carnitine chloride)p-xylilene diester; bis (decanoyl-L-carnitine chloride; bis(decanoyl-D-carnitine chloride); bis(dodecanoyl-L-carnitine chloride); and bis (dodecanoyl-D-carnitine chloride).

6. A pharmaceutical composition comprising a compound of formula (I):

$$\text{(I)}$$

wherein:
R is a straight or branched, saturated or unsaturated alkanoyl group having 2–16 carbon atoms;
Y is a straight of branched alkylene chain having 3–6 carbon atoms, or ortho, meta or para-xylilene; and
X is a anion of a pharmacologically acceptable acid; and
a pharmacologically acceptable excipient thereof.

7. A composition of claim 6, comprising a compound of Formula (I) from 0.5 to 2% by weight and a pharmacologically acceptable excipient thereof.

8. A method for treating a cutaneous or mixed cutaneous infection comprising application of a pharmaceutical composition of claim 6 to an infected tissue.

9. A composition of claim 7 or 8, wherein said composition is selected from the group consisting of a cream, ointment, gel, lotion and a solution.

10. A process for preparing a compound of formula (I):

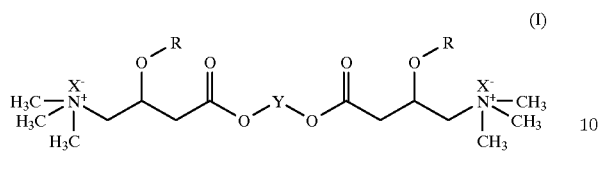
(I)

wherein:

R is a straight or branched, saturated or unsaturated alkanoyl group having 2–16 carbon atoms;

Y is a straight of branched alkylene chain having 3–6 carbon atoms, or ortho, meta or para-xylilene; and X is a anion of a pharmacologically acceptable acid;

which comprises the steps of:
(a) suspending an alkonoyl L-carnitine inner salt in an organic, anhydrous inert solvent [such as N,N-dimethylformamide, acetonitrile or methylene chloride];
(b) adding to the suspension at 0° C.–10° C. a compound of formula Z-Y-Z wherein Y is as defined above and Z is selected from the group consisting of halogen, O-mesyl and O-tosyl in an amount equivalent to one half of the moles of the alkanoyl L-carnitine;
(c) keeping the suspension under stirring at 20° C.–50° C. for 24 hours until the suspension is completely solubilized;
(d) precipitating the reaction raw product by adding a solvent;
(e) filtering off the product and washing with acetone or methylethylketone until a solid product is obtained;
(f) dissolving the product in water;
(g) eluting on a strongly basic resin to obtain a salified product;
(h) lyophilizing the eluate;
(i) purifying the solid of step (g) by chromatography on $C_8$ silica; and,
(j) eluting with $H_2O/CH_3N$ 70:30;

wherein a compound of formula (I) is prepared.

11. A process for preparing a compound of formula (I):

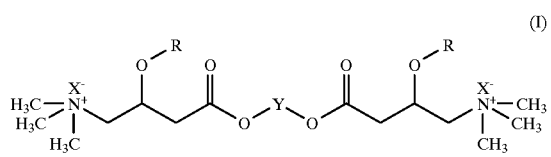
(I)

wherein:

R is a straight or branched, saturated or unsaturated alkanoyl group having 2–16 carbon atoms;

Y is a straight of branched alkylene chain having 3–6 carbon atoms, or ortho, meta or para-xylilene; and X is a anion of a pharmacologically acceptable acid;

which comprises the steps of:
(a) suspending the alkonoyl L-carnitine acid chloride in an organic, anhydrous inert solvent;
(b) adding to the suspension at room temperature a compound of formula Z-Y-Z wherein Y is as described above and Z is OH in an amount equivalent to one half of the moles of the alkanoyl L-carnitine;
(c) keeping the suspension under stirring at room temperature for 16–24 hours until the suspension is completely solubilized;
(d) concentrating the solution to dryness under vacuum;
(e) purifying the raw product thus obtained by silica gel chromatography;
(f) eluting with $H_2O/CH_3CN$ solutions; and
(f) isolating the compound by concentration and subsequent lyophilization;

wherein a compound of formula (I) is prepared.

* * * * *